United States Patent
Booker

[11] Patent Number: 5,821,749
[45] Date of Patent: Oct. 13, 1998

[54] RELUCTANCE CHANGE APPARATUS AND METHOD OF DETECTING LOSS OF CROSS-SECTIONAL AREA OF MAGNETIC METALLIC STRENGTH MEMBERS USED IN CONDUCTORS SUCH AS ALUMINUM CONDUCTOR STEEL REINFORCED ("ACSR") CONDUCTORS

[76] Inventor: James R. Booker, 11718 Walnut Hill Dr., Baltimore, Ohio 43105

[21] Appl. No.: 510,198

[22] Filed: Aug. 2, 1995

[51] Int. Cl.$^6$ ............................ G01N 27/82; G01N 27/90
[52] U.S. Cl. ............................ 324/240; 324/228; 324/262
[58] Field of Search ................................. 324/220–221, 324/228–230, 239, 240, 241, 242, 243, 262

[56] References Cited

U.S. PATENT DOCUMENTS

| | | | |
|---|---|---|---|
| 2,057,835 | 10/1936 | Karajan et al. | 324/229 |
| 2,897,438 | 7/1959 | Fearon | 324/221 |
| 3,241,057 | 3/1966 | Rall | 324/243 X |
| 4,070,625 | 1/1978 | Harpster | 324/239 |
| 4,218,651 | 8/1980 | Ivy | 324/262 |
| 4,546,316 | 10/1985 | Lang | 324/240 X |
| 4,827,215 | 5/1989 | van der Walt | 324/242 X |
| 5,321,356 | 6/1994 | Weischedel | 324/262 |
| 5,357,198 | 10/1994 | Ando et al. | 324/242 |

FOREIGN PATENT DOCUMENTS

| | | |
|---|---|---|
| 921556 | 2/1973 | Canada ................................. 324/228 |
| 0116765 | 8/1984 | European Pat. Off. . |
| 0216628 | 4/1987 | European Pat. Off. . |
| 0 228 644 | 7/1987 | European Pat. Off. . |
| 0 235 030 | 9/1987 | European Pat. Off. . |
| 0 271 670 | 6/1988 | European Pat. Off. . |
| 0298303 | 1/1989 | European Pat. Off. . |
| 0316206 | 5/1989 | European Pat. Off. . |
| 0 321 111 | 6/1989 | European Pat. Off. . |
| 0 321 112 | 6/1989 | European Pat. Off. . |

OTHER PUBLICATIONS

Nondestructive Testing Handbook 2nd Edition, pp. 632–651, vol. 4; 1986.

(List continued on next page.)

Primary Examiner—Gerard R. Strecker
Attorney, Agent, or Firm—Francis T. Kremblas, Jr.

[57] ABSTRACT

A method and apparatus for detecting a loss in cross-sectional area of metallic reinforcing members having magnetic properties of a conductor indicating corrosion effects on the conductor. The method and apparatus comprises a tug component to provide the motive force to move a data collection component and a detector component along a length of conductor. The tug component further includes a rechargeable battery, a motor energizable by the rechargeable battery, a guide wheel and tensioner assembly. Linked to the tug is a data collection component. In turn, a detector is linked to the data collection unit. The tug, data collection unit and detector all ride along the same conductor by a series of guide wheels and tensioners. The detector further includes a magnetic source spaced apart from an electronic coil winding. In use, a conductor is interpositioned between the magnetic source and electronic coil winding. The magnetic source is preferably energized to produce a rotating magnetic field which is directed at the conductor. The amount of magnetic field passing through the conductor corresponds to the cross-sectional area of the steel reinforcing strands of a conductor. The magnetic field recognized by the coil induces a varying voltage depending upon the cross-sectional area of the steel strands of the conductor through which the rotating magnetic field passes. The electronic coil may also be linked to a recording system such that the change in magnetic field induces a change in voltage in the coil which can be recorded on a strip chart, graph, CPU or other suitable data collection unit. The data collection component therefore may also include a relay system comprising a transmitter and receiver sufficient to send data streams and information to a ground surface when the unit is used above ground to analyze and test overhead conductors.

18 Claims, 4 Drawing Sheets

OTHER PUBLICATIONS

Advertisement by Cormon, Ltd for "Overhead Line Corrosion Detector" (no date).

Advertisement by Telog data recorders R–2100 Series (no date).

Article: Parts I & II; Havard et al., "AGED ACSR Conductors", IEEE; vol. 7, No. 2, Apr. 1992 pp. 581–594.

Article: CIGRE, Aug. 28—Sep. 3, 1994 Session by Delree et al. pp. 1–7, "Inspection Policy . . . Experience".

Article: CIGRE 1986, "Some Investigations of the Ageing of Overhead Lines", Maddock et. al.

Article: J.M. Ferguson et al., Overhead Transmission Lines—Refurbishment and Developments, Power Engineering Journal, Jun. 1994, pp. 109–118.

RELUCTANCE CHANGE APPARATUS AND METHOD OF DETECTING LOSS OF CROSS-SECTIONAL AREA OF MAGNETIC METALLIC STRENGTH MEMBERS USED IN CONDUCTORS SUCH AS ALUMINUM CONDUCTOR STEEL REINFORCED ("ACSR") CONDUCTORS

BACKGROUND OF THE INVENTION

1. Field of the Invention

The present invention relates generally to methods and apparatuses for detecting degradation of metallic conductors including, but not limited to, steel reinforced conductors, but more particularly to detecting a loss of cross-sectional area of the conductor or the steel reinforcing members of steel reinforced conductors due to the effects of corrosion, natural and industrial contamination and aging.

2. Description of the Related Art

Systems for the transformation of other types of energy (e.g., hydro, steam, etc.) into electrical energy, and the transmission of this electrical energy to the point of consumption may be referred to generally as electric power systems. Alternating current (AC) is generally used in modern power systems, because it may be easily converted to higher or lower voltages by means of transformers thereby enabling each stage of the electric power system to be operated at an appropriate voltage.

A typical electric power system consists of several principle elements including: the power station; a set of transformers to raise the generated power to the high voltages used on the transmission lines; the transmission lines; the substations at which the power is stepped down to the voltage on the sub-transmission lines; the sub-transmission lines; and the transformers that lower the sub-transmission voltage to the level used by the consumer's equipment.

In a typical system, the generators at the central power station typically deliver a voltage of from 1,000 to 26,000 volts (V). Higher voltages are usually undesirable because of difficulties of insulation and the danger of electrical breakdown and damage. This voltage is stepped up by means of transformers to values ranging from 138,000 V (138 Kilovolts or "KV") to 765,000 V (765 KV) for the primary transmission line (the greater the voltage on the line, the less the current and consequently the less the power loss, the loss being proportional to the square of the current).

At the substation, the voltage may be transformed down to levels of 69 KV to 138 KV for further transfer on the sub-transmission system to yet another set of transformers which steps the voltage down to a distribution level such as 2.4, 4.2, 15, 27 or 33 Kilovolts (KV). Finally, the voltage is transformed once again at the distribution transformer near the point of use to 240 V or 120 V (i.e., 110 volt household voltage). Thus, the central station of a power system consists of a prime mover, such as a water or steam terminal, which operates an electric generator.

A key component of the overall system, in order to transmit the power generated at the system to the end user or consumer, is the high voltage transmission line or sub-transmission line. The lines of high voltage transmission systems are usually composed of wires of copper, aluminum, copper clad or aluminum clad steel, which are suspended from a tall lattice work tower of steel by strings of porcelain insulators. By the use of clad steel wires and high towers, the distance between towers can be increased, and the cost of the transmission line thus reduced. In modern installations with essentially straight paths, high voltage lines may be built with, for example, as few as four towers to the mile (e.g., a 765 KV line). In some areas, high voltage lines are suspended from tall wooden poles spaced more closely together. For lower voltage sub-transmission and distribution lines, wooden poles are generally preferred rather than steel towers.

Long transmission lines have considerable inductance and capacitance as well as resistance. When a current flows through the lines, inductance and capacitance have the effect of carrying the voltage on the line as the current varies. Thus, the supply voltage varies with the load. Several kinds of devices are used to overcome this undesirable variation, in an operation called regulation of the voltage. The concept of electrical induction discovered by British Physicist Michael Faraday has been defined as the creation of an electric current in a conductor moving across a magnetic field. A similar, but inverse concept is the concept of reluctance.

Reluctance is the opposition offered in a magnetic circuit to a magnetic flux, but more specifically, is the ratio of the magnetic potential difference to the corresponding flux. Thus, a change in the conductor density, material, or other factors would affect the induction of electricity as well as present a reluctance change with respect to the aforementioned transmission and sub-transmission lines of a electrical power system. A change in inductance and reluctance is commonly associated with the degradation of the conductor due to such things as corrosion and age.

The art to which the invention relates includes an apparatus and method of detecting galvanization loss on steel conductors or steel components of conductors. Such an overhead line galvanization detector has been referred to as a corrosion detector which is actually a misnomer because galvanization loss is believed to by some to merely mark the beginning of a corrosion cycle. In actuality, however, it has been shown that galvanization of steel members used in a water or other corrosive environments (e.g., considering the galvanic cell conditions created by water and metallic conductor components) has little if any effect as a corrosion retardant. One such device for detecting galvanization loss is a device called an "Overhead Line Corrosion Detector" marketed by Cormon LTD. of West Sussex in the United Kingdom.

The Cormon device and method of detecting galvanization loss includes an apparatus configured to rest on, engage, and travel along a transmission line or overhead conductor. The Cormon device incorporates a first drive component commonly referred to as a "tug" coupled to a data transmission unit. Both units are designed to be powered by rechargeable batteries. A detector head is coupled or linked to the data transmission unit and is pulled along with the assembly by the tug.

The tug component, therefore, serves merely as the motive force to pull the detection components along the length of the conductor (i.e., the data collection unit and the cylindrical collar-like detector head are moved along the conductor by the motorized tug). A transmitter is associated with the data collection unit and is believed to employ an RF data carrier signal to send the data collected by the detector head to a ground station or central processing unit (CPU).

The detector head or sensing head as it is referred to by Cormon is a hollow cylinder which clamps around the conductor. It contains a field winding and a pickup coil. When high frequency current is passed through the field winding, it generates a magnetic field surrounding the conductor. The magnetic field surrounding the conductor penetrates the conductor and induces eddy currents around the individual strands as the sensing head is pulled along the conductor.

The alternating flux induces a voltage in the pickup coil which is processed to give an in phase and quadrature output voltage, the magnitudes of which depend on the quality of the galvanized layer. Thus, the voltage differences realized by the pickup coil are attributable to the eddy currents induced within conductor as the sensing head is moved along the conductor. The detected voltage differences are correlated to the loss of galvanization through a series of algorithms, the manipulation of which is carried out by the CPU.

It is known that the Cormon device does not detect loss of cross-sectional area of steel reinforcing members of overhead conductors despite the name given the device by Cormon.

Considering the useful life of an overhead conductor is believed to be within the range of 10–80 years, and considering that many of the steel reinforced overhead conductors found in the United States, and many other countries of the world, were put in service in the 1930's and 1940's, it is particularly important to be able to determine the remaining useful life of such conductors. In addition, considering the extraordinary high cost of replacing such conductors and the attendant liability associated with energized conductor failure (i.e., conductors falling from their towers) it would be advantageous to invent a device capable of detecting the loss of cross-sectional area of steel reinforcing members of a conductor in a power transmission or sub-transmission line attributable to corrosion of the steel members. The reliability of the power system would be greatly enhanced if the near failures could be replaced before failure.

Canadian Patent Number 921556, incorporated by reference as if fully set forth herein is directed to a method and associated apparatus for the electrical detection of flaws in materials. The Canadian device incorporates a plurality of current carrying coils which are placed beside the material to be tested. Some of the coils are then energized, and the resultant effect is detected by a pick up coil. The Canadian device differs significantly in structure and function from the apparatus and method of the present invention.

U.S. Pat. No. 4,218,651 granted to Ivy, incorporated by reference as if fully set forth herein, is directed to an apparatus for detecting longitudinal and transverse imperfections in elongated ferrous work pieces. The Ivy device differs significantly in structure and function from the apparatus and method of the present invention.

U.S. Pat. No. 2,897,438 granted to Fearon, incorporated by reference as if fully set forth herein, is directed to a casing joint detector. The Fearon invention is similar to the Ivy and Canadian devices, and it too differs significantly in structure and function from the apparatus and method of the present invention.

Accordingly, until now, there is no known method to measure the loss of cross-sectional area of steel reinforcing members of a conductor in a power transmission or sub-transmission line attributable to corrosion of the steel members.

SUMMARY OF THE INVENTION

The present invention is an apparatus and method for detecting a loss of cross-sectional area of steel strength members in aluminum conductor steel reinforced conductors commonly referred to as "ACSR" conductors. Of course, the present invention may also be utilized in conjunction with other types of conductors which incorporate steel members for added strength, wherein the steel members are subject to corrosion, natural and industrial contamination, aging, and thus associated strength losses.

The present invention is also useful for determining the loss of cross-sectional area of a shield or static line which are not energized. While structurally similar to lines associated with energized conductors, shield or static lines are essentially ground lines used in conjunction with overhead electrical distribution and transmission lines to effectively ground the electrical energy associated with lightening strikes and the like.

The apparatus of the present invention includes a motive component, a data collection component and a detecting component different in structure and function from the art to which the invention relates. The motive component which will also be referred to hereinafter as a tug component is comprised of a motor, a power source to energize the motor, and a series of guide wheels which maintain the tug component in proper motive alignment with the conductor. All of the tug components are attached to a common or interconnected housing.

The data collection component and detector components are pulled along the conductor by the tug. Thus, when the tug component is actuated, its drive system turns enabling the tug to drive the entire assembly (tug, data collection component and detector) along the conductor.

One of the key components of the invention is, therefore, the detector. The detector includes a pulley-like wheel which maintains the proper alignment of the detector elements with the conductor. The detector also includes an electronic coil winding positioned adjacent to and in close approximation to the conductor when the detecting unit rests or is in operable engagement therewith. In this manner, the pulley wheel is preferably sized to correspond to a wide range of conductors yet allow the coil to maintain a predetermined optimal separation distance from the conductor to be analyzed. Opposite the coil and conductor to be analyzed is a source of rotational magnetic field. In this manner, the conductor is interpositioned between the coil and a rotating magnetic field.

The magnetic field generating component of the preferred embodiment resembles a horseshoe or similar bi-polar magnet having oppositely designated poles for positive and negative charges. The magnetic source is rotated by an oscillating component which may be a simple motor sufficient to enable the horseshoe-like magnetic field inducing magnetic to rotate at an optimal predetermined rate of rotation.

When energized, the motor spins the magnet about a central axis interpositioned between the poles. The spinning magnet induces a rotating, oscillating ("twisting") magnetic field which impinges upon the conductor interpositioned between the magnetic field and generating device and the coil. Of course, the separation distance of the magnetic source and the conductor is preselected and may be adjusted according to the thickness of the conductor being analyzed. The coil, positioned on the opposite side of the conductor (recall the conductor is interpositioned between the twisting magnetic field and the coil) detects the magnetic field passing through the conductor. The detected magnet field induces a voltage in the coil. The amount of voltage detected by the coil is recorded, and is known to be inversely related to the cross-sectional area of the steel reinforcing members within the conductor.

In the preferred embodiment the data collection component sends the data bit stream on to a ground station or CPU.

An RF carrier wave may be used as the medium to send the signal to the ground station or CPU where the incoming data stream may be recorded and illustrated by an oscilloscope type screen, strip chart, or stored magnetically.

The invention may also incorporate a voltage recording device to record the maximum and minimum voltages experienced (i.e., induced) by the coil winding. That is, a preferred recorder may also be a voltage meter capable of recording and storing maximum and minimum voltage information to enable the user to more efficiently extrapolate the usefull life data of the conductor.

For example, the voltage induced into the coil for a "fresh" conductor (i.e., a conductor having a cross-sectional area equal to a new conductor as measured at the beginning of its useful life) could be a minimum baseline value. The voltage induced into the coil for a conductor of similar configuration with a known cross-section at the point of failure may be recorded as the maximum. Thus, if a conductor under test (an "aged" conductor, i.e., a conductor having a cross-sectional area measured at some time after the beginning of its useful life) were to induce voltage near the maximum value, the user may determine that a failure is imminent. Similarly, if the voltage associated with the test sample was below the maximum, and the time the conductor was in service was known, then the user may extrapolate to a point in time where imminent failure were to occur.

In use, when the apparatus is towed along a length of conductor by the tug component, the detector may induce a voltage in the coil as described above. For example, if an air space (conductor absent) were interpositioned between the magnetic field generating component and the coil, a base line voltage would be induced into the coil and recorded. If a conductor was interpositioned between the magnetic field generating device and the coil, and the conductor is free of defects in the steel strands, the cross-sectional area of the steel strands would be 100% which would correspond to a second baseline voltage.

The disparity between the first and second baseline voltages creates the continual on which a loss of cross-sectional area of the steel reinforcing strands or the integrity thereof can be measured. For example, if a length of aged or partially degraded conductor were interpositioned between the magnetic field generating device and the coil, a third baseline voltage would be recorded. This third baseline would fall somewhere between the first and second baseline values corresponding to 0% steel strands and 100% steel strands, respectively. Thus, the relative loss of cross-sectional area of the steel reinforcing strands would be detected and calculated.

If the inventive device was moved along a length of conductor, the varying voltages would yield critical information as to the existence, or lack thereof, of weak portions of the conductor due to a loss of the cross-sectional area of the steel reinforcing strands of the conductor. In this manner, it is conceivable that the user may accurately determine where an imminent failure of the conductor might occur. Furthermore, studies have shown that in a typical conductor having nineteen steel strands, if the cross-sectional area of the steel strands was to fall below the equivalent of seven (7) full "healthy" strands, a serious failure condition exists.

Thus, the method of the present invention is closely associated with the operation of the apparatus of the present invention in the manner in which the loss in cross-sectional area of the steel strength members of the conductor affect the conductor's efficiency as well as provide the user with a means to identify where and perhaps when a failure might occur in the conductor.

This method of detection, while closely associated with corrosion of the steel reinforcing strands may also be utilized to detect steel strands which are inferior in production and, therefore, create a weak link in the conductor and transmission line chain when initially installed or manufactured. This type of information may be particularly useful if one were to use the apparatus of the present invention and perform the method of the present invention to calculate and monitor usefull life information of a variety of conductors from a point in time when they are first installed to a projected date of eventual failure.

This information may also be particularly useful to help the power industry budget for the great expense associated with replacing conductors and therefore possibly eliminate the unnecessary expense of prematurely replacing conductors which still possess a quantitatively significant useful life.

To that end, it is important to point out the distinction between the invention and the art to which the invention relates. For example, with respect to the Cormon device described above, a loss of galvanization provides no insight as to the loss of the integrity of the steel strength members, eventual failure, or any indication as to when a conductor must be repaired or replaced. Recall, loss of galvanization is believed to be the starting point at which corrosion might occur, but provides no information whatsoever as to the existing strength or lack thereof of the steel reinforcing members associated with the conductors.

The present invention may be summarized in a variety of ways, one of which is the following: a detector for detecting a loss of cross-sectional area in a conductor having at least one metallic reinforcing member, comprising: an attachment plate; a source of magnetic energy operatively mounted to the attachment plate and configured to emanate a magnetic field; a coil winding operatively mounted to the attachment plate spaced apart from the rotatable magnetic source to define a receiving space therebetween, wherein the receiving space is configured to receive a conductor to enable the magnetic field to induce a measurable voltage within the coil winding even when the conductor is positioned in the receiving space and interpositioned between the source of magnetic energy and the coil winding.

The detector may further include a drive element to impart a rotational torque to the source of magnetic energy to cause the magnetic field to rotate; a recorder to record the voltage induced in the coil winding, an electrical connection means for electronically interconnecting the recorder to the coil winding, and a transmitter and a receiver to transmit information voltage information from the coil to the recorder by a radio frequency carrier signal and without the need for wiring to interconnect the recorder to the coil winding. The at least one metallic reinforcing member is at least partially comprised of a material selected from the group of materials consisting of steel, steel alloy, copper, and iron.

The detector may further include a housing to cover the coil winding and the source of magnetic energy, a power source for energizing the drive element, and wheel means for positioning the detector on a conductor. The source of magnetic energy may further comprise a magnet having a positive pole substantially parallel to a negative pole.

The present invention may also be summarized as follows: a system for detecting a loss of cross-sectional area in a conductor having at least one metallic reinforcing member, comprising: a detector component; a data transmission component; a tug linked to the detector component and the data transmission component; drive means for supplying power to the tug, detector component and data transmission component, to enabling them to travel along a conductor; the detector further includes a source of magnetic energy configured to emanate a magnetic field and direct the magnetic field toward a coil winding spaced apart from the source of magnetic energy to define a receiving space therebetween, and enabling the coil winding to experience an induced voltage in response to the source of magnetic energy even when a conductor is positioned within the receiving space.

The electrical connection means of the system may further include a transmitter and a receiver to transmit voltage information from the coil to the recorder by a radio frequency carrier signal and without the need for wiring to interconnect the recorder to the coil winding.

The present invention may also be summarized as follows: a method of detecting a loss of cross-sectional area of a conductor having a length and at least one metallic reinforcing member, the method comprising the steps of: providing a detector having a source of magnetic energy configured to emanate a magnetic field, a coil winding spaced apart from the source of magnetic energy to provide a receiving space for a conductor to be interpositioned therebetween, and wherein the coil winding is configured to experience an induced voltage in response to the magnetic field; positioning a conductor in the receiving space interpositioned between the source of magnetic energy and the coil winding; energizing the detector; and recording the voltage induced in the coil winding.

The inventive method may also include providing a drive element to impart a rotation torque to the source of magnetic energy to cause the source of magnetic energy to rotate and emanate a rotating magnet field, providing a wheel means for positioning the detector on a conductor, moving the detector along the length of the conductor. The step of recording the voltage may further include the step of: transmitting the voltage information recorded by the recorder to a receiving station by a radio frequency carrier signal.

The present invention may also be summarized as follows: a method of forecasting the useful life of a conductor having at least one metallic reinforcing member based on a known minimum cross-sectional area, wherein the conductor has at least one metallic reinforcing member, comprising the steps of: providing a detector for measuring the cross-sectional area of the at least one metallic reinforcing member; measuring and recording the cross-sectional area of the at least one metallic reinforcing member at the beginning of the life of a conductor; measuring and recording the cross-sectional area of the at least one metallic reinforcing member at any time after the beginning of the life of a conductor; comparing the recorded cross-sectional area of the at least one metallic reinforcing member taken at the beginning of the life of a conductor to the cross-sectional area of the at least one metallic reinforcing member taken at any time after the beginning of the life of a conductor; determining the amount of loss in cross-sectional area of the at least one metallic reinforcing member and determining the amount of time that has passed between the measurement of the cross-sectional area of the conductor at the beginning of the useful life of the conductor and the measurement of the cross-sectional area of the conductor after the beginning of useful life of the conductor; and extrapolating from the combination of: (i) the amount of lost cross-sectional area of the conductor and the amount of time determined to have passed that is associated with the loss of cross-sectional area, and (ii) the known minimum cross-sectional area of the conductor, to determine the useful life of the conductor.

Therefore, numerous objects, features and advantages of the present invention exist, and only a sample of those objects, features and advantages are set forth herein.

It is an object of the present invention to provide an apparatus for detecting corrosion in a conductor.

It is an object of the present invention to provide an apparatus for detecting a loss in cross-sectional area of a conductor wherein such loss is associated with corrosion, natural and industrial contamination, and aging.

It is an object of the present invention to provide an apparatus for detecting strength loss due to corrosion or other degradation of a conductor.

It is an object of the present invention to provide an apparatus for detecting a loss in strength of a conductor.

It is an object of the present invention to provide an apparatus to assist in the prediction of the useful life of a conductor.

It is an object of the present invention to provide an apparatus for assisting in the determination as to when a conductor should be replaced or repaired.

It is an object of the present invention to provide a system for recording the relative location of the loss of strength of steel reinforcing members of a conductor.

These and other objects, features and advantages shall become apparent after consideration of the scope of the specification and drawings set forth herein. All such objects, features and advantages are part of and contemplated as within the scope of the present invention even though not specifically set forth.

DETAILED DESCRIPTION OF THE PREFERRED EMBODIMENT(S)

Figure 1:
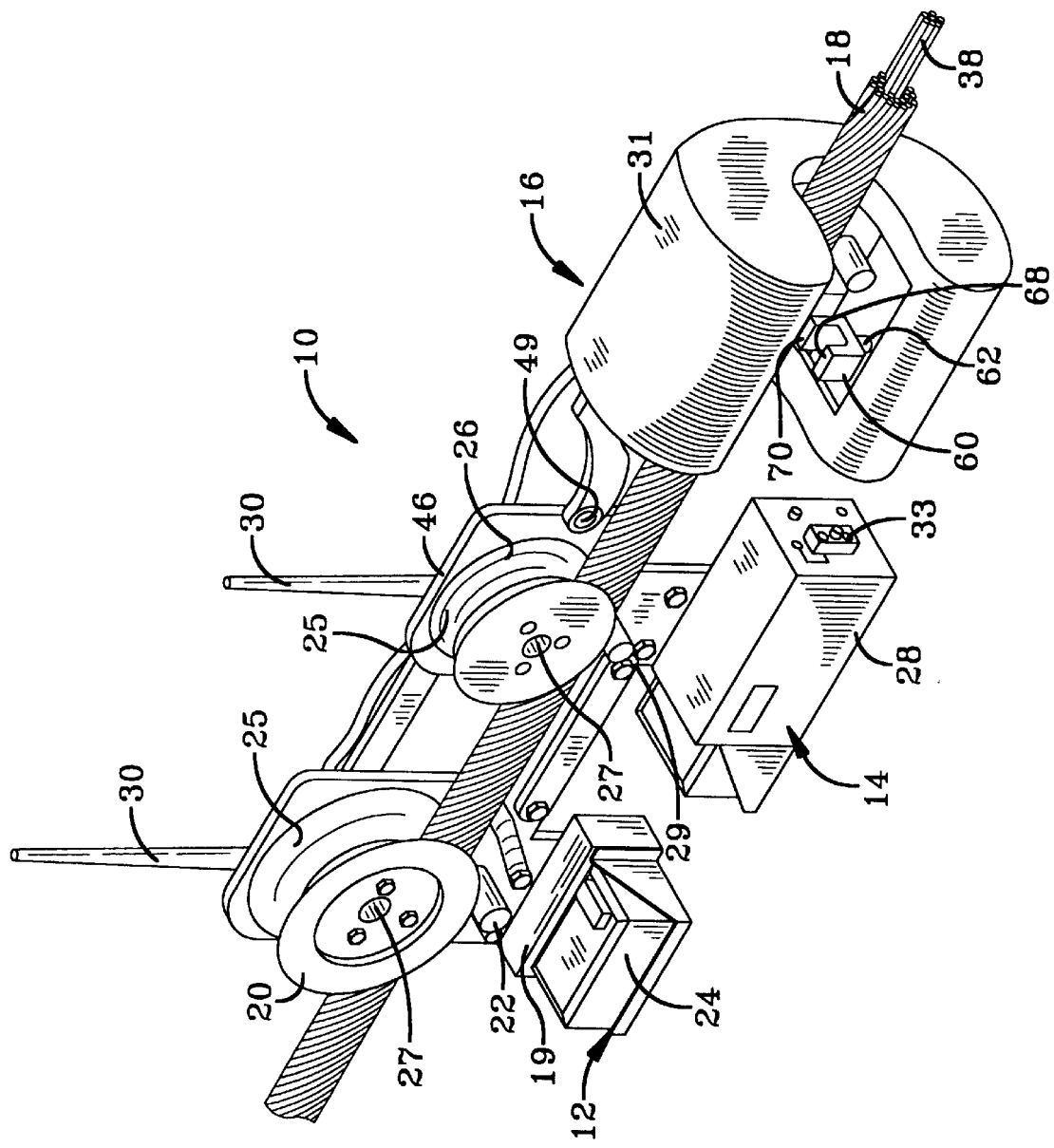
FIG. 1 is an elevated perspective view of an embodiment of the present inventive apparatus.

With reference to FIG. 1, an embodiment of the present invention is designated generally by the reference numeral 10. Embodiment 10 includes a tug component 12, a data collection and transmission component 14, and a detector designated generally by the reference numeral 16.

An embodiment of the tug component 12, data transmission component 14, and detector component 16 are operatively positioned on a conductor 18. Tug component 12 includes a housing 19, a guide wheel 20 and tensioner 22 to maintain the tug in communication with the conductor 18 during operation. A rechargeable battery 24 is provided to power the tug and provide the energy to power a drive motor (not shown) within the housing 19 sufficient to provide the electromotive force necessary to move the system along the conductor 18. The drive motor may be remotely controlled from the ground when the invention is used on an overhead conductor.

With respect to the collection and transmission component 14, a pulley wheel 26 and tensioner 29, similar to that provided with the tug component 12, is provided to maintain the detector in communication with the conductor 18. The guide wheel 20 and pulley wheel 26 have a trough 25 formed around their circumference like a conventional pulley wheel to enable the conductor 18 to rest therein and be interpositioned between the guide wheel 20 and tensioners 22 in the manner indicated in FIG. 1 in order to hold the conductor and tug in operative alignment therewith during use. The guide wheel 20 and pulley wheel 26 have a conventional axle 27 as shown in FIG. 1 enabling them to rotate around it. Similarly, with respect to FIG. 2, axle 27 enables the pulley wheel 50 to rotate it, and the hitch 44 to be attached thereto in the manner shown in the Figure. A transmitter (not shown) is contained within the housing box 28 houses the internal components necessary to transmit data to a ground station or CPU (not shown). Antennas 30 provide the means through which signal transmission may be accurately achieved. An electrical connection 33 may also be provided to enable the exchange of electrical signals between components such as the relay of data from the detector 16 to the collection/transmission unit 14 or some other mechanism for recording data such as a CPU or strip chart recorder.

Tug 12 and data transmission component 14 may be of any suitable configuration but preferably is substantially similar or identical to the tug and data transmission component associated with the overhead line corrosion detector manufactured and sold by Cormon of West Sussex in the United Kingdom, and described above.

Figure 2:
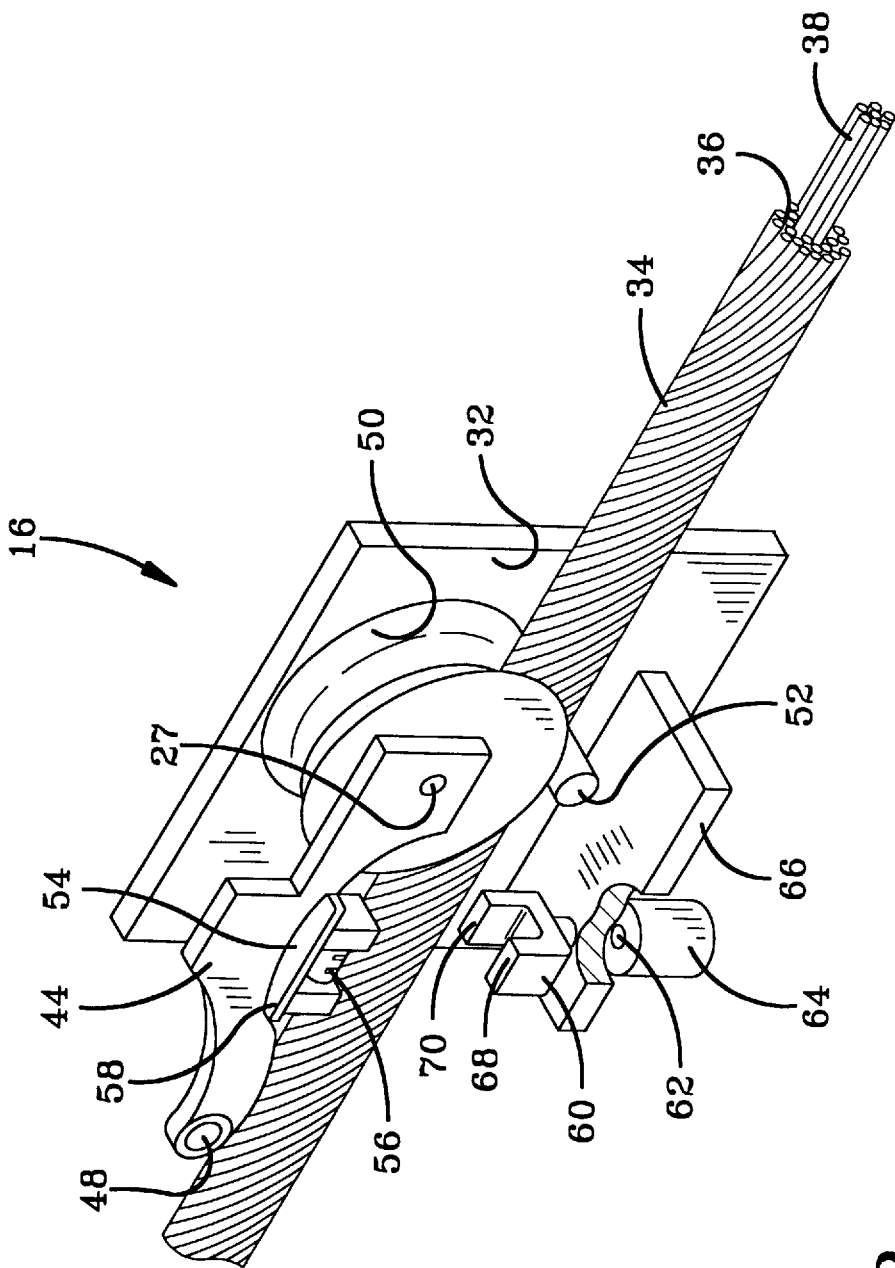
FIG. 2 is an elevated perspective view of the detector component of an embodiment of the present invention shown in FIG. 1.

With reference to the detector 16, attention is now directed to FIGS. 1 and 2. Detector 16 includes a shielded housing 31 supported by and covering a baseplate 32 onto which several components may be mounted. A conductor 34 (18 in FIG. 1) is shown in relative operable alignment with the detector 16. The conductor 34 further includes a plurality of twisted strands 36 and 38 typically made from aluminum and steel, respectively.

It is important to note that the detector 16 of FIGS. 1 and 2 is the same. The housing of FIG. 1 covers the detector in that figure. The hitch 44 emerges from the housing in the manner shown in FIG. 1 and is attached to the detector in the manner shown in FIG. 2. The hitch is shown bent in both FIGS. 1 and 2 in order to align it with the axis of the conductor, but other suitable configurations are allowable. The detector rests on the conductor as shown in FIG. 2, and it is pulled by the tug of FIG. 1 by linking the detector to the tug by the connection of the hitch 44 to the rear plate 46 and the detector component. The housing is simply a shroud for the detector and is attached to the baseplate 32. The coil is operatively supported by this plate by virtue of the attachment to the hitch in the manner shown.

Steel strands 38 provide the reinforcement necessary to the center of the conductor 34 to attain certain strength characteristics. That is, the steel strands 38 form the reinforcement of the core of the conductor 34 over which the aluminum strands 36 are wrapped.

Figure 3:
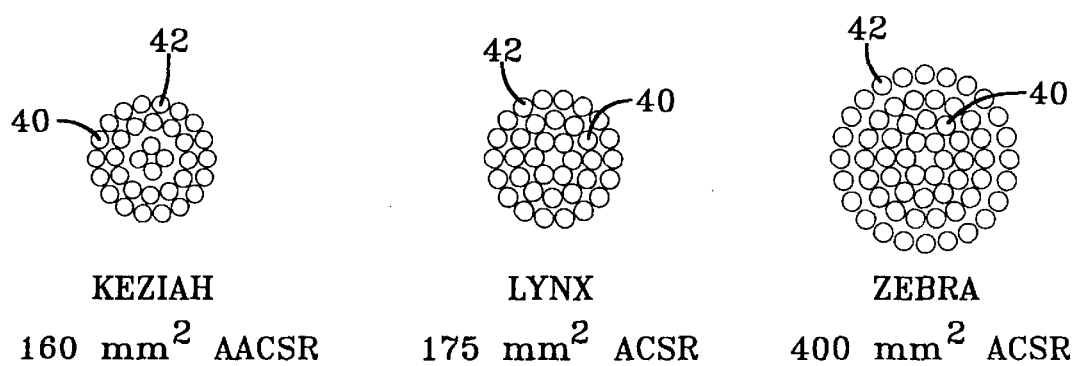
FIG. 3 is a representational cross-sectional view of several conventional ACSR conductors.

With brief reference to FIG. 3, several aluminum conductor steel reinforced (ACSR) conductors are illustrated in cross-section. The central starred configuration 40 is formed from the steel reinforcing strands 38 of FIG. 2. The outer circles indicate the cross-sectional area of the aluminum strands 42 corresponding to strands 36 of FIG. 2. Thus, it is common to provide a steel reinforced core consisting of seven tightly wound steel strands 40. The number of steel strands can be easily detected by counting the points from the star-like configuration of the core and considering a central strand is interpositioned between each of the points of the starred configuration.

Irrespective of the number of aluminum strands, and depending upon the size of the conductor used; it is common that ACSR conductors include one, seven, and nineteen strands surrounded by the aluminum strands to provide the added strength necessary for the conductor to maintain its integrity.

With reference to FIG. 2, a hitch 44 is provided as part of the detector 16. Hitch 44 attaches to the rear plate 46 and to the detector 16 shown in FIG. 1. Thus, a preferred configuration of the hitch 44 includes a central aperture 48 through which a pivot pin 49 may be inserted to pivotally attach the hitch 44 to the data collection component 14 enabling it to be pulled along behind it by the tug 12 as it moves along the conductor 18 (or 34 in FIG. 2).

Attached to the hitch 44 is a pulley-like wheel 50 opposite a locking tensioner 52. The combination of the pulley 50 and locking tensioner 52 enables the conductor 34 to be operatively interpositioned therebetween and maintain an optimum contact enabling the detector to consistently and efficiently ride along conductor 34.

The detector 16 further includes a coil winding assembly 54. The coil winding assembly 54 includes a coil 56 and core 58. In addition, a magnetic source 60 is spaced apart and opposite from the coil 54 (and conductor 34). The coil assembly 54 may be rigidly attached or formed to be a part of the hitch 44 as shown in FIG. 2. Magnetic source 60 includes a central axis which is parallel to a central shaft 62 which in turn is operably attached to a motor 64. Motor 64 provides a rotational torque to the shaft 62 enabling the magnetic source 60 to turn at an optimum rate of rotation.

A mounting plate 66 is provided to enable the magnetic source 60, shaft 62 and motor 64 to be operatively attached to the baseplate 32, and interposition of the conductor 34 between the coil 56 and magnetic source 60.

Figure 4A:
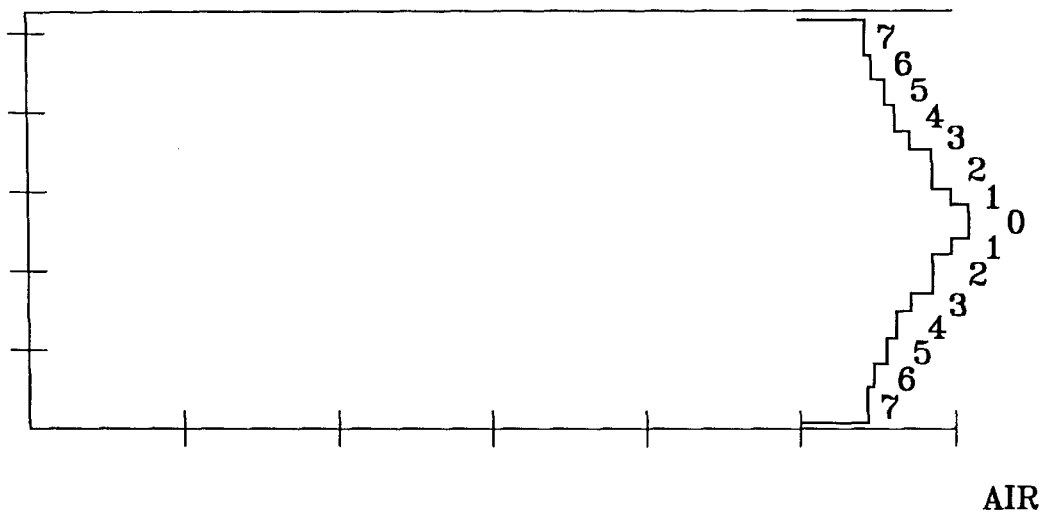
FIGS. 4A and 4B are strip chart printouts illustrating the resultant data collected by an embodiment of the present invention after actual use.
Figure 4B:
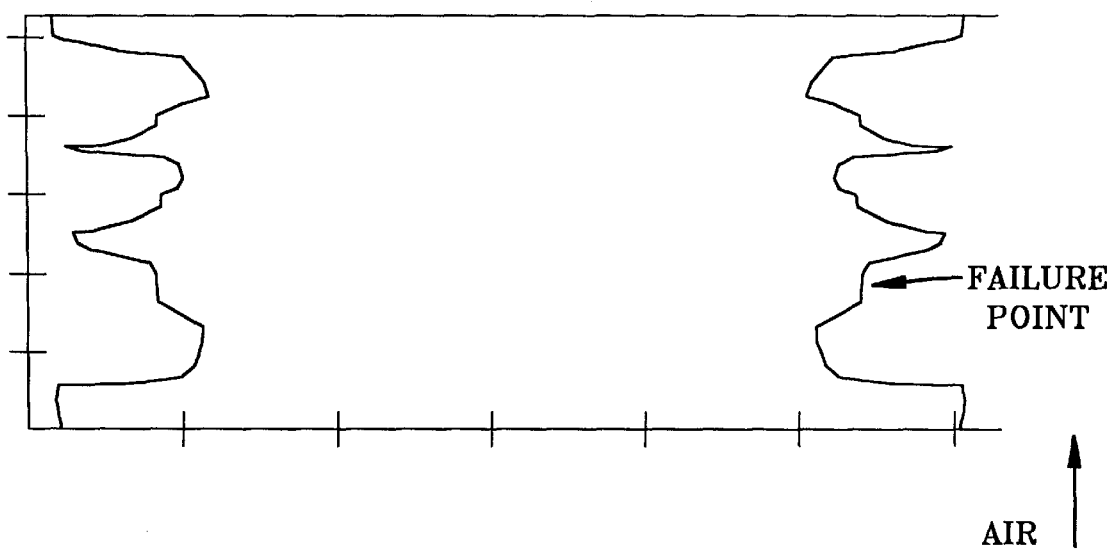

With reference to FIGS. 2 and 4 for an exemplary description of the utility of the invention, a baseline reference of the recorded data printed out on a strip chart (FIG. 4) is formed by energizing the motor 64 enabling the magnetic source 60 to rotate. When this occurs, a rotating or twisting magnetic field emanating from the opposing poles 68 and 70 of the magnetic source 60 induces a voltage in the coil 54. The induced voltage is recorded on a strip chart for graphical representation and visual identification.

If the conductor 34 were absent from the space between the magnetic source 60 and coil 56, a strip chart printout of a certain width corresponding to the zero of Part A of FIG. 4 would result. It is important to mention that Part A and Part B of FIG. 4 is an actual strip chart of the operation of the device taken when an ACSR conductor having steel reinforcing strands is passed between the magnetic component 60 and coil 56 of the detector 16.

Referring to the width markings on the strip chart designated by the numeral "0" indicating that zero steel strands are present, the "0" width marking accurately corresponds to the baseline reading for air. As strands are added to the conductor the strip chart printout changes. For example, when one steel strand is added, denoted by the numeral "1", such that there are six strands missing, the strip chart nearly approximates the zero or baseline level for air, but is notably different. Similarly, the numerals "2" through "7" correspond to the number of steel strands present, with "7" denoting a complete conductor with seven steel reinforcing strands present. The strip chart printout for a seven steel strand conductor is the smallest corresponding to a notably lower voltage induced in the coil 54.

With reference to Part B of FIG. 4, it is important to point out that the conductor being measured is a 345 KV line splice failure with 19 internal steel strands. It was determined through testing that of the nineteen (19) steel strands present in the conductor, the conductor failed when the cumulative cross-sectional area of the steel strands was less than the cross-sectional area associated with seven steel strands in a new condition. That is, while many of the original strands were present or simply broken at certain places, the cumulative cross-sectional area of all nineteen strands was less than seven "fresh" strands. As can be determined from Part B of the figure, the peaks of the strip chart correspond to the location on the conductor when the cross-sectional area was equal to seven strands. Similarly, where the valleys appear on the strip chart, they correspond to a substantially fresh segment of conductor having nineteen steel strands. However, as can be determined by the strip chart, even the nineteen strand portion of the conductor does not dip to the level of the new conductor, thus it can be concluded that a minute loss in cross-sectional area had occurred.

These and other embodiments, and equivalents, of the present invention shall become apparent after consideration of the specification and drawings. All such alternate embodiments and equivalents are believed to be, and are contemplated as, part of the present invention whose only limitation is the scope of the appended claims.

What is claimed is:

1. A system for detecting a loss of cross-sectional area in a conductor having at least one metallic reinforcing member having magnetic properties, comprising:

a detector component;

a data transmission component;

a tug linked to the detector component and the data transmission component to pull the detector component along the conductor;

drive means for supplying power to the tug, to enable the detector component to travel along a conductor in response to the pulling force of the tug to which it is linked;

the detector component further includes a rotatably mounted source of magnetic energy configured to emanate a rotating magnetic field and direct the magnetic field toward a coil winding spaced apart from the source of magnetic energy to define a receiving space therebetween, and enabling the coil winding to experience an induced voltage in response to the magnetic field when said conductor is positioned within the receiving space.

2. The system of claim 1, wherein:

the at least one metallic reinforcing member having magnetic properties and partially comprised of a material selected from the group of materials consisting of steel, iron, nickel, and cobalt.

3. The system of claim 1 further comprising:

a drive element to impart a rotational torque to the source of magnetic energy to cause the magnetic field to rotate.

4. The system of claim 1, further including:

a recorder to record the voltage induced in the coil winding.

5. The system of claim 4, further including:

connection means for electronically interconnecting the recorder to the coil winding.

6. The system of claim 5, such that the connection means further includes:

a transmitter and a receiver to transmit information voltage information from the coil to the recorder by a radio frequency carrier signal and without the need for wiring to interconnect the recorder to the coil winding.

7. The system of Claim 1, further including:

a housing to cover the coil winding and the source of magnetic energy.

8. The system of claim 3, further comprising:

a power source for energizing the drive element.

9. The system of claim 1, such that the source of magnetic energy further comprises:

a magnet having a positive pole substantially parallel to a negative pole.

10. The system of claim 1, further including:

wheel means for positioning the system on a conductor.

11. A method of detecting a loss of structural strength of a generally cylindrical conductor having a length supported above ground level between two fixed points and at least one metallic reinforcing member having magnetic properties extending along the length of said conductor, the method comprising the steps of:

providing a detector unit including a rotatably mounted source of magnetic energy configured to emanate a rotating magnetic field, a coil winding spaced apart from the source of magnetic energy to provide a receiving space for said generally cylindrical conductor, and wherein the coil winding is configured to experience an induced voltage in response to the magnetic field;

supporting said detector unit on said conductor for longitudinal movement along the length of said conductor with said conductor disposed in a predetermined position in said receiving space between said source of magnetic energy and said coil; rotating the source of magnetic energy; causing said detector unit to be moved along the length of said conductor while maintaining said predetermined position of said conductor in said receiving space relative to said source of magnetic energy and said coil and recording the voltage induced in the coil winding by the rotating source of magnetic energy as said detector unit is moved along said conductor.

12. The method of claim 11, wherein said detector unit is movably supported on said conductor between a rolling wheel and guide, both of which are mounted to said detector unit.

13. The method defined in claim 11 wherein said conductor includes a plurality of discrete metallic reinforcing strands having magnetic properties and arranged in a generally cylindrical configuration having an axis parallel to the length of said conductor and wherein said induced voltage is indicative of the residual structural strength of said cylindrical configuration formed by said strands.

14. An apparatus for detecting the loss of the structural strength of a conductor having a length and at least one generally cylindrical metallic member having magnetic properties extending along the length of said conductor, comprising in combination;

an attachment plate;

a detector unit including a rotatably mounted source of magnetic energy operatively mounted to said plate and configured to emanate a rotating magnetic field and a coil winding mounted to said plate and spaced from said source of magnetic energy to define a receiving space between said source of magnetic energy and said coil configured to receive said conductor in a spaced relationship between said source of magnetic energy and said coil winding;

a mounting component connected to said attachment plate and configured to engage said conductor in force-transmitting, movable engagement to support said attachment plate and said detector unit for longitudinal movement along said conductor and maintain the relative position of said conductor in said receiving space between said source of magnetic energy and said coil winding;

a motive force operatively connected to said attachment plate to cause said attachment plate to move longitudinally along said conductor; and a voltage recorder operatively connected to said coil winding to measure the voltage induced in said coil winding by a rotating magnetic field emanating from said source of magnetic energy.

15. The apparatus defined in claim 14 wherein said rotatably mounted source of magnetic energy is a permanent magnet.

16. The apparatus defined in claim 14 wherein said detector unit further includes a radio frequency transmitter operatively connected to said coil winding to enable voltage data to be transmitted to a recorder remote from said detector unit.

17. The apparatus defined in claim 14 wherein said conductor includes a plurality of reinforcing members comprising a plurality of discrete metallic strands having magnetic properties arranged to form a generally cylindrical configuration.

18. The apparatus defined in claim 15 wherein said permanent magnet has a positive and a negative pole disposed at generally a right angle to the longitudinal axis of said conductor.

* * * * *